United States Patent [19]

Mikkelsen et al.

[11] Plant 4,726

[45] May 26, 1981

[54] KALANCHOE PLANT

[75] Inventors: James C. Mikkelsen; Cornelis P. Van den Berg, both of Ashtabula, Ohio

[73] Assignee: Mikkelsens Inc., Ashtabula, Ohio

[21] Appl. No.: 134,114

[22] Filed: Mar. 26, 1980

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Koch

[57] ABSTRACT

A kalanchoe plant known by the cultivar name Yellow Nugget, and particularly characterized by its uniform deep yellow flower color, on both its top and under sides; excellent branching; dense foliage, and by its adaptability to growth in various pot sizes.

1 Drawing Figure

1

The present invention relates to a new and distinctive variety of Kalanchoe plant, botanically known as a *Kalanchoe blossfeldiana Poelln* and referred to by the cultivar name Yellow Nugget.

Yellow Nugget was discovered by us as a mutation of Golden Nugget, a commercial but unpatented cultivar. Golden Nugget is a mutation of Nugget, disclosed in U.S. Plant Pat. No. 4,207 to James C. Mikkelsen. Asexual reproduction by stem cuttings has shown that the unique features of this new Kalanchoe are stabilized and are reproduced true to type in successive propagations.

The following characteristics distinguish Yellow Nugget from both its parent varieties and other cultivated Kalanchoes of this type known and used in the floriculture industry:

1. Generally speaking, Yellow Nugget is similar to Nugget, except for flower color.

2. The flower color of Yellow Nugget, both top side and under side, is deep yellow, as contrasted with the parent cultivar Golden Nugget which exhibits a red infusion on the under side of the petals.

3. Uniform coloration of the petals of Yellow Nugget gives an even yellow coloring of the flowering cyme.

4. Cultivar has excellent branching, similar to Nugget.

5. Foliage is dense, small, with a tendency to bend or twist along the main vein.

6. Growth rate, leaf size and self-branching makes cultivar suitable for production in pot sizes from 10 to 15 cm.

7. Flowering time is 10 weeks in summer to 14 weeks in winter, after start of short days.

The accompanying colored photograph illustrates the overall appearance and color of Yellow Nugget. The photograph is a top view and shows the colors as true as it is reasonably possible to obtain in a color reproduction of this type.

The following is a detailed description of Yellow Nugget, based on plants produced under commercial practices in the greenhouses of Mikkelsens Inc., Ashtabula, Ohio. Color references are made to the Royal Horticultural Society Colour Chart except where general terms of ordinary dictionary significance are used.

Parentage: Mutation of Golden Nugget, which is in turn a mutation of Nugget.

Propagation:

2

(A) *Type cutting.*—Short tip cutting with stems up to 2 cm. long.

(B) *Time to root.*—10 days at 21° C. summer; 14 days at 21° C. winter.

(C) *Rooting habit.*—Fibrous, many very fine roots.

Plant description:

(A) *Form.*—Short, compact, and upright. Growing and scheduling practices can produce either a small plant in a 10 cm. pot or a larger plant in a 15 cm. pot.

(B) *Habit of growth.*—Rate of growth moderate for this type of plant. Under optimum conditions shoots are formed at every node.

(C) *Foliage description.*—Leaves simple, opposite. (1) Size: Average full grown leaf of a flowering plant in a 10 cm. pot is 90 mm. long × 70 mm. wide. Plants in larger pots have leaves up to 120 mm. long × 100 mm. wide. (2) Shape: Ovate to elliptic, apex obtuse, base obtuse to attenuate. Foliage has a tendency along the main vein to bend or twist. (3) Texture: Glabrous, coriaceous, succulent. (4) Margin: Slightly crenate. (5) Color: Young foliage, top side green 137A, under side green 137C. Mature foliage, top side yellow-green 147A, under side green 137C.

Flowering description:

(A) *Flowering habits.*—Inflorescence of each shoot is formed by dichotomous branching, starting with opening of terminal flower of main axis, followed by terminal flowers of the side branches, continuing with subsequent development of branches in the inflorescence.

(B) *Natural flowering season.*—Mid-January. Flowering time under controlled daylength at 20° C. in summer is 10 weeks; in winter 14 weeks. Flowering time depends on temperature, light intensity and other growing conditions.

(C) *Flower bud description.*—Elliptical to oblong, up to 12 mm. long, developing to tubular as flower petals mature, sheathed with four green sepals; corolla at maturity 10 mm. long.

(D) *Flowers borne.*—On compound dichasial cymes. The primary peduncle is 4–5 mm. in diameter, with peduncle length depending on growing conditions and B9 application; pedicels up to 6 mm. long.

(E) *Quantity of flowers.*—Highly floriferous; main axis counted 80 open flowers, side branches counted 30 open flowers, with 4–8 side branches in a 10 cm. pot plant.

(F) *Petals.*—(1) Shape: Nearly round, top cuspidate. (2) Color: Top side when opening yellow 12B, fading to yellow-orange 15C, under side yellow-orange 14C. (3) Number of petals: Four (4), united in corolla, salverform. Petals 6 mm. in diameter and total flower diameter 14–15 mm.

(G) *Reproductive organs.*—(1) Stamens: Eight (8) in number. (a) Anther shape: flat, elliptical; color yellow. (b) Filament color: light green. (c) Pollen color: yellow. (2) Pistels: (a) Stigma shape: flat, crystalline; color, greenish white. (b) Style color: light green. (c) Ovaries: 4 celled, 8 mm. long; color, light green.

Disease resistance: No diseases observed to date. Cultivar is highly resistant to mildew.

We claim:

1. A new and distinct cultivar of Kalanchoe plant known by the cultivar name Yellow Nugget, as described and illustrated, and particularly characterized by its uniform deep yellow flower color, on both its top and under sides; excellent branching; dense foliage, and by its adaptability to growth in various pot sizes.

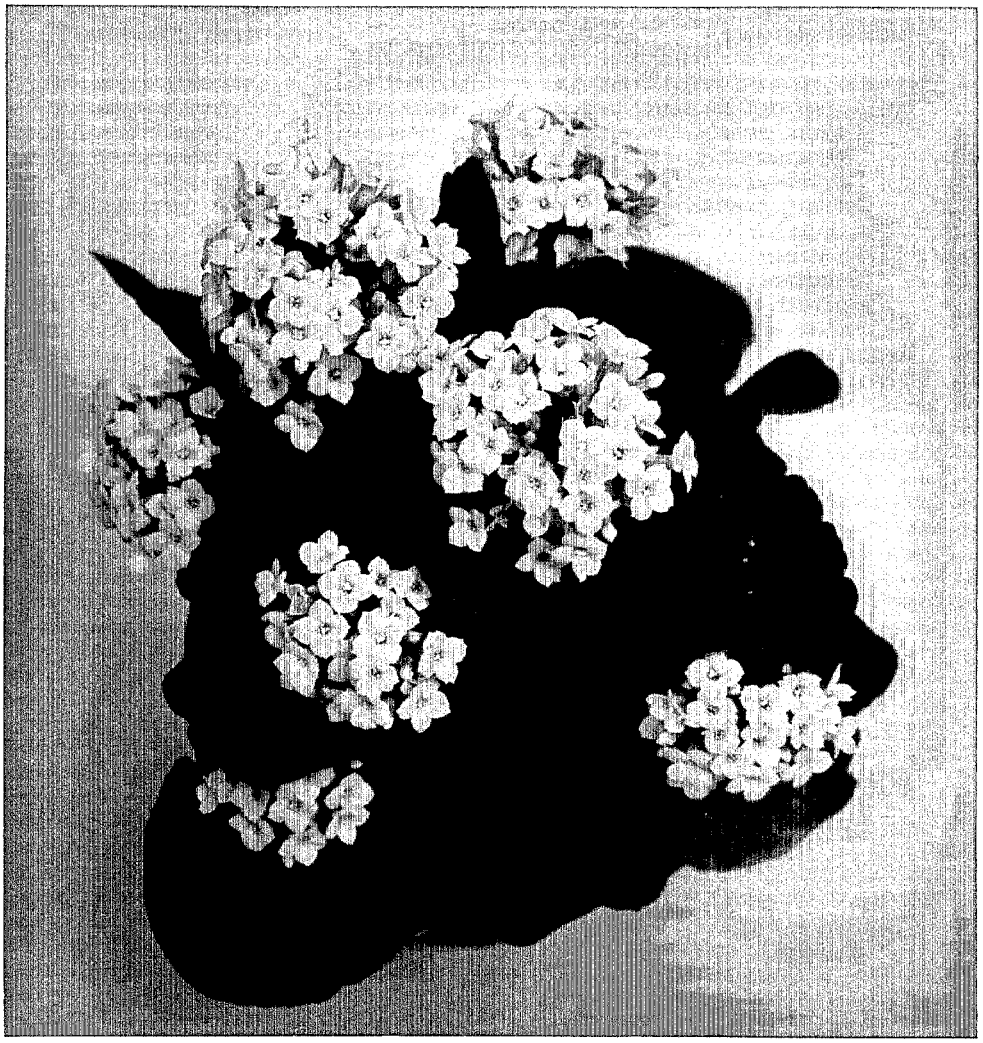

* * * * *